(12) United States Patent
Mahmood et al.

(10) Patent No.: US 8,798,725 B2
(45) Date of Patent: Aug. 5, 2014

(54) METHOD FOR DETERMINING A HEART PERIOD FROM AN ECG WAVEFORM USING IMAGE REPRESENTATION OF ECG

(75) Inventors: Tanveer Syeda Mahmood, Cupertino, CA (US); Fei Wang, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 13/592,123

(22) Filed: Aug. 22, 2012

(65) Prior Publication Data

US 2012/0316452 A1    Dec. 13, 2012

Related U.S. Application Data

(63) Continuation of application No. 12/714,020, filed on Feb. 26, 2010.

(51) Int. Cl.
*A61B 5/04* (2006.01)
*A61B 5/02* (2006.01)

(52) U.S. Cl.
CPC ........................................ *A61B 5/02* (2013.01)
USPC ........................................................ 600/509

(58) Field of Classification Search
CPC ............ A61B 5/02; A61B 5/04; A61B 5/024; A61B 5/044; A61B 5/0402
USPC ........................................................ 600/509
See application file for complete search history.

(56) References Cited

U.S. PATENT DOCUMENTS

| 4,989,610 | A | 2/1991 | Patton et al. |
|---|---|---|---|
| 5,012,411 | A | 4/1991 | Policastro et al. |
| 6,056,691 | A | 5/2000 | Urbano |
| 6,086,537 | A | 7/2000 | Urbano et al. |
| 6,228,030 | B1 | 5/2001 | Urbano et al. |
| 6,438,411 | B1 * | 8/2002 | Guttman et al. ............... 600/521 |
| 6,592,522 | B2 | 7/2003 | Bjaerum et al. |
| 6,782,121 | B2 * | 8/2004 | Badilini ........................ 382/128 |
| 7,181,054 | B2 | 2/2007 | Zaleski |
| 7,424,137 | B2 | 9/2008 | Badilini |
| 2005/0169509 | A1 | 8/2005 | Grasslin |
| 2006/0173336 | A1 * | 8/2006 | Goubergen ................... 600/450 |
| 2006/0264769 | A1 | 11/2006 | Satin |

FOREIGN PATENT DOCUMENTS

WO    WO2008001258 A2    3/2008

OTHER PUBLICATIONS

Syeda-Mahmood et al ., "Shape Based Matching of ECG Recordings", international IEEE Conference on Engineering in Medicine and biology (EMBC2007),pp. 2012-2018, Aug. 23-26, 2007.*
Bhullar et al."A computer Based system for the study of QT intervals", Computers in cardiology 1991, proceedings pp. 533-536.*

(Continued)

*Primary Examiner* — Christopher D Koharski
*Assistant Examiner* — Roland Dinga
(74) *Attorney, Agent, or Firm* — Shimokaji & Associates, P.C.

(57) ABSTRACT

A method for estimating a heart period is disclosed. The heart period is detected from an ECG recording. ECG data is acquired, and converted into electronic ECG images. The data is processed to prepare for estimation of a heart period. The heart period is estimated based upon an average of intervals between a plurality of detected peaks of electronic electrocardiogram waveforms. The peaks are determined by taking a product of a filtered electronic ECG signal with a wandering baseline removed, a difference between the upper and lower ECG envelopes of the electronic ECG images, and a first order derivative of a derived ECG waveform.

10 Claims, 6 Drawing Sheets

(56) References Cited

OTHER PUBLICATIONS

Nicky Kern, Bernt Schiele, Albrecht Schmidt; Recognizing context for Annotating a Live Life Recording, Pers Ubiquit Comput (2007) 11: 251-263, DOI 10.1007/s00779-006-0086-3, Received Oct. 30, 2003, Accepted Jun. 1, 2005, Published online Aug. 16, 2006, Springer-Verlag London Limited.

Chandrajit Bajaj, Samrat Goswami; Multi-Component Heart Reconstruction From Volumetric Imaging, SPM 2008, Stony Brook, New York, Jun. 2-4, 2008., Association for Computing Machinery, Inc.

Cristano M. Agulhari, Rosanna M. R. Silvera, Ivan S. Bonatti; Compressing Electrocardiogram Signals Using Parameterized Wavelets, SAC 08 Mar. 16-20, 2008, Fortaleza,Cear'a, Brazil, Association for Computing Machinery, Inc.

"Mathematical Morphology", http://en.wikipedia.org/wiki/Mathematical_morphology, captured on Jun. 14, 2009.

Office Action dated May 3, 2013 in related U.S. Appl. No. 12/714,020.

Office Action dated Sep. 25, 2013 in related U.S. Appl. No. 12/714,020.

* cited by examiner

METHOD FOR DETERMINING A HEART PERIOD FROM AN ECG WAVEFORM USING IMAGE REPRESENTATION OF ECG

RELATED APPLICATIONS

The present continuation application claims benefit of U.S. application Ser. No. 12/714,020, filed on Feb. 26, 2010, which application is incorporated herein by reference in its entirety.

BACKGROUND OF THE INVENTION

The present invention relates generally to the field of electrocardiograms (ECG), and more specifically, automatic processing of electrocardiograms.

There has been an increased need for automatic processing of the electrocardiogram (ECG). Many systems have been developed to perform signal processing tasks such as 12-lead off-line ECG analysis, and real-time patient monitoring. These applications require an accurate detection of the heart rate by the ECG.

Although many hospitals now have digital ECG records, much of the ECG data is in paper form. Unlocking these ECG records printed on paper and exposing them to digital analysis would be useful.

Digital ECG recordings are sampled finely, and contain noisy data with baseline wandering problems. The heart beats that illustrate a disease may be carefully screened by technicians before taking the recording, so that the paper version may show only a few seconds of data needed for diagnosis While it is difficult to estimate the heart cycle directly from a depicted heart region in a video, it is relatively easy to estimate the heart rate from a synchronizing ECG.

Hence, there is a need for a method and apparatus for determining a heart period using image representation obtained from an ECG.

SUMMARY OF THE INVENTION

In one aspect of the invention, a method for estimating a heart period using at least one of a plurality of electrocardiogram recordings is disclosed. The method comprises utilizing a computer processor to obtain the plurality of electrocardiogram recordings generated from a plurality of electrocardiogram sources; converting the plurality of the electrocardiogram recordings into a plurality of corresponding electronic electrocardiogram images; removing noise from the corresponding electronic electrocardiogram images; deriving an electrocardiogram waveform from one of the electronic electrocardiogram images by extracting an upper envelope and a lower envelope of the electrocardiogram waveform from the corresponding electronic electrocardiogram image using a curve tracing algorithm, the algorithm for extracting the upper envelope and lower envelope comprising: tracing upper and lower edges of a curve of the electrocardiogram waveform from one of the electronic electrocardiogram images; defining two search ranges centered around the upper and lower edges of the curve of the electrocardiogram waveform; using at least one of: a morphological open algorithm to fill in holes inside the curve of the electrocardiogram waveform and a morphological close algorithm to eliminate noise pixels near the curve of the electrocardiogram waveform; closing small gaps by closing the electrocardiogram waveform between inserted seed points along an expected location of the electrocardiogram waveform; and closing large gaps by inserting a segment tangent to the curve of the electrocardiogram waveform; determining an electrocardiogram signal peak from increased thickness at the electrocardiogram signal peak due to pixel dithering; determining a difference between the upper envelope and the lower envelope at the electrocardiogram signal peak and at an electrocardiogram low point, which represent a local maximum and a local maximum and a local minimum of one of the corresponding electronic electrocardiogram images; estimating the heart period by: computing a first order derivative of the derived electrocardiogram waveform for amplifying high frequencies of the derived electrocardiogram waveform; determining a peak of the derived electrocardiogram waveform by taking a product of a filtered electrocardiogram signal from one of the corresponding electronic electrocardiogram images, with a wandering baseline removed, a difference between the upper envelope and the lower envelope of the derived electrocardiogram waveform from each of the at least one of the corresponding electronic electrocardiogram images and the first order derivative of the derived electrocardiogram waveform; and determining an average of intervals between a plurality of detected peaks from at least one region selected from the derived electrocardiogram waveform; and outputting the determined heart period on a user interface display.

In another aspect, a system for estimating a heart period using at least one of a plurality of electrocardiogram recordings is disclosed. The system comprises an electrocardiogram machine utilizing a computer processor to obtain at least one of the plurality of electrocardiogram recordings generated from at least one of a plurality electrocardiogram sources; a conversion machine for converting said at least one electrocardiogram recording into a corresponding electronic electrocardiogram image; a de-noising machine for removing noise from the corresponding electronic electrocardiogram image; a derivation machine for deriving an electrocardiogram waveform from the corresponding electronic electrocardiogram image, by extracting an upper envelope and a lower envelope of the derived electrocardiogram waveform from the electronic electrocardiogram image using a curve tracing algorithm, the algorithm for extracting the upper envelope and lower envelope comprising: tracing upper and lower edges of a curve of the electrocardiogram waveform from the corresponding electronic electrocardiogram image; defining two search ranges centered around the upper and lower edges of the curve of the electrocardiogram waveform; using a morphological open algorithm to fill in holes inside the curve of the electrocardiogram waveform; using a morphological close algorithm to eliminate noise pixels near the curve of the electrocardiogram waveform; closing small gaps by closing the electrocardiogram waveform between inserted seed points along an expected location of the electrocardiogram waveform; and closing large gaps by inserting a segment tangent to the curve of the electrocardiogram waveform; the derivation machine further determining an electrocardiogram signal peak from increased thickness at the electrocardiogram signal peak due to pixel dithering; the derivation machine further determining the difference between the upper envelope and the lower envelope at the electrocardiogram signal peak and at an electrocardiogram low point, which are a local maximum and a local minimum of the derived electrocardiogram waveform from the corresponding electronic electrocardiogram image; an estimation machine for: computing a first order derivative of the derived electrocardiogram waveform for amplifying high frequencies of the derived electrocardiogram waveform; determining a peak of the derived electrocardiogram waveform by taking a product of a filtered electrocardiogram signal from the corresponding electronic electrocardiogram image in which a wandering baseline has been removed, a difference between the upper envelope and the lower envelope of the derived electrocardiogram waveform in the corresponding electronic electrocardiogram image and the first order derivative of the derived electrocardiogram waveform; and estimating the heart period as an average of intervals between a plurality of detected peaks from the at least one simultaneously selected region from each of the plurality of electronic electrocardiogram images and from the derived electrocardiogram waveform; and a user interface display for outputting the estimated heart period.

In a further aspect, a processor implemented computer program product for estimating a heart period using at least one of a plurality of electrocardiogram recordings is disclosed. The computer program product comprises: computer program code performing on a computer processor in an electrocardiogram machine measuring electrical activity of a heart for: obtaining obtaining at least one of a plurality of electrocardiogram recordings generated from at least one of a plurality of electrocardiogram sources; converting at least one electrocardiogram recording into a corresponding electronic electrocardiogram image; removing noise from the corresponding electronic electrocardiogram image; deriving an electrocardiogram waveform from the corresponding electronic electrocardiogram image, by extracting an upper envelope and a lower envelope of the derived electrocardiogram waveform from the electronic electrocardiogram image using a curve tracing algorithm, the algorithm for extracting the upper envelope and lower envelope comprising: tracing upper and lower edges of a curve of the electrocardiogram waveform from the corresponding electronic electrocardiogram image; defining two search ranges centered around the upper and lower edges of the curve of the electrocardiogram waveform; using a morphological open algorithm to fill in holes inside the curve of the electrocardiogram waveform; using a morphological close algorithm to eliminate noise pixels near the curve of the electrocardiogram waveform; closing small gaps by closing the electrocardiogram waveform between inserted seed points along an expected location of the electrocardiogram waveform; and closing large gaps by inserting a segment tangent to the curve of the electrocardiogram waveform; and determining an electrocardiogram signal peak from increased thickness at the electrocardiogram signal peak due to pixel dithering; determining a difference between the upper envelope and the lower envelope at the electrocardiogram signal peak and at an electrocardiogram low point which are a local maximum and a local minimum of the derived electrocardiogram waveform from the corresponding electronic electrocardiogram image; estimating the heart period, by: computing a first order derivative of the derived electrocardiogram waveform for amplifying high frequencies of the derived electrocardiogram waveform; determining a peak of the derived electrocardiogram waveform by taking a product of a filtered electrocardiogram signal from the corresponding electronic electrocardiogram image with a wandering baseline removed, the difference between the upper envelope and the lower envelope of the derived electrocardiogram waveform in the corresponding electronic electrocardiogram image, and the first order derivative of the derived electrocardiogram waveform; and estimating the heart period, as an average of intervals between a plurality of detected peaks from the derived electrocardiogram waveform; and outputting the estimated heart period on a user interface display.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention may estimate a heart period based on an image representation of an ECG waveform. It may be used, for example, in diagnosing arrhythmia patients.

The present invention differs from the prior art in using images for detecting periodicity in ECG waveforms. The invention transforms all ECG information into images, and uses the waveform images to determine heartbeat periodicity.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

As will be appreciated by one skilled in the art, exemplary embodiments of the present invention may be embodied as a system, method or computer program product. Accordingly, exemplary embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction performing system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as JAVA (JAVA is a registered trademark of Sun Microsystems), Smalltalk™, C++ or the like and conventional procedural programming languages, such as the "C" programming language or similar programming languages. The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Exemplary embodiments of the present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which perform via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which perform on the computer or other programmable apparatus provide processes for implementing the functions/acts specified in the flowchart and/or block diagram block or blocks.

Exemplary embodiments of the present invention are related to techniques for a method and apparatus for determining a heart period using image representation obtained from an ECG.

Figure 1:
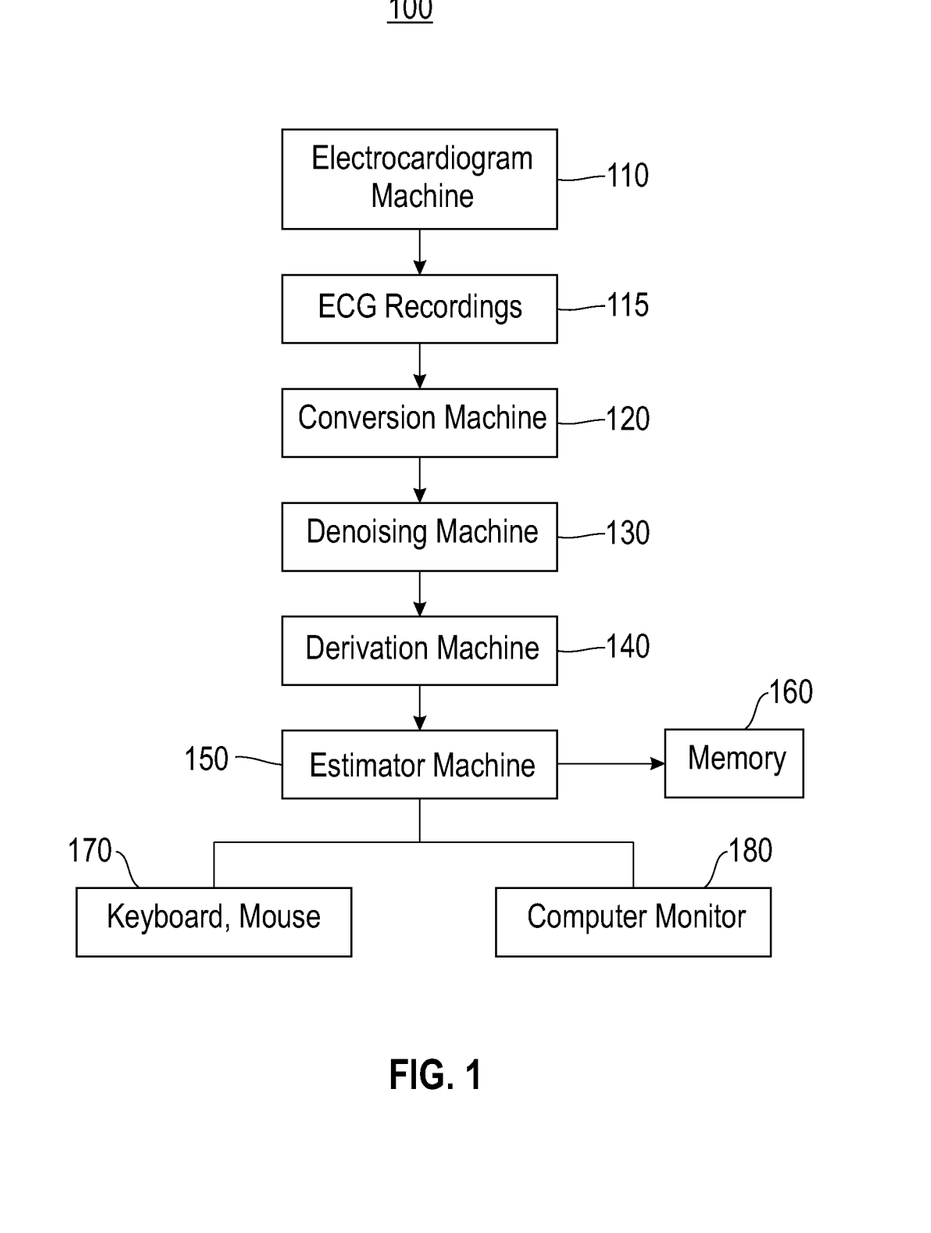
FIG. 1 is a block diagram of a system according to one exemplary embodiment of the invention.

FIG. 1 is a block diagram of a system 100 for estimating a heart period using a plurality of electrocardiogram recordings according to an exemplary embodiment of the invention. The system 100 may include an Electrocardiogram Machine 110, a Conversion Machine 120, a De-noising Machine 130, a Derivation Machine 140, an Estimator Machine 150, a memory 160, a keyboard and a mouse input 170, and a user interface display, such as a computer monitor 180.

An electrocardiogram machine 110 may utilize a computer processor to obtain a plurality of electrocardiogram recordings generated from a plurality of electrocardiogram sources. In one case, the user may utilize the invention by receiving electrocardiogram recordings 115 from an electrocardiogram machine 110 and inputting them into a conversion machine 120. The conversion machine 120 may be a scanner for converting paper electrocardiogram recordings into electronic electrocardiogram image form. The conversion machine 120 may also be an electronic converter for converting the paper electrocardiogram from the electrocardiogram machine 110 into an electronic image for display on a computer monitor 180. The conversion machine 120 may further convert the digital electrocardiogram waveforms into corresponding electronic electrocardiogram images. The conversion machine 120 may further remove a wandering baseline from these digital ECG waveforms. A wandering baseline, as is known in the art is a signal pattern that wanders across a screen, which may be caused by unsatisfactory electrode connections. The conversion machine 120 may further comprise a converter for converting an echocardiogram into an electronic electrocardiogram using electrocardiogram regions of interest detection.

The De-noising machine 130 may remove noise from the electronic electrocardiogram images.

The Derivation machine 140 may derive an electrocardiogram waveform by extracting an upper envelope and a lower envelope of the electrocardiogram waveform from the electronic electrocardiogram images using a curve tracing algorithm described in more detail below. A difference between the upper envelope and the lower envelope of an electrocardiogram waveform from a selected region of an electronic ECG image may signify a local maximum and a local minimum of the electrocardiogram waveform from one of the corresponding electronic electrocardiogram images.

The Derivation machine may further determine an electrocardiogram signal peak from increased thickness at the electrocardiogram signal peak due to pixel dithering. The difference between the upper envelope and the lower envelope may increase at an electrocardiogram signal peak, and at an electrocardiogram low point.

The estimation machine 150 may estimate the heart period, and a user may use a keyboard or a mouse 170 to output the estimated heart period on a computer monitor 180. The estimated heart period may be stored in memory 160.

Figure 2:
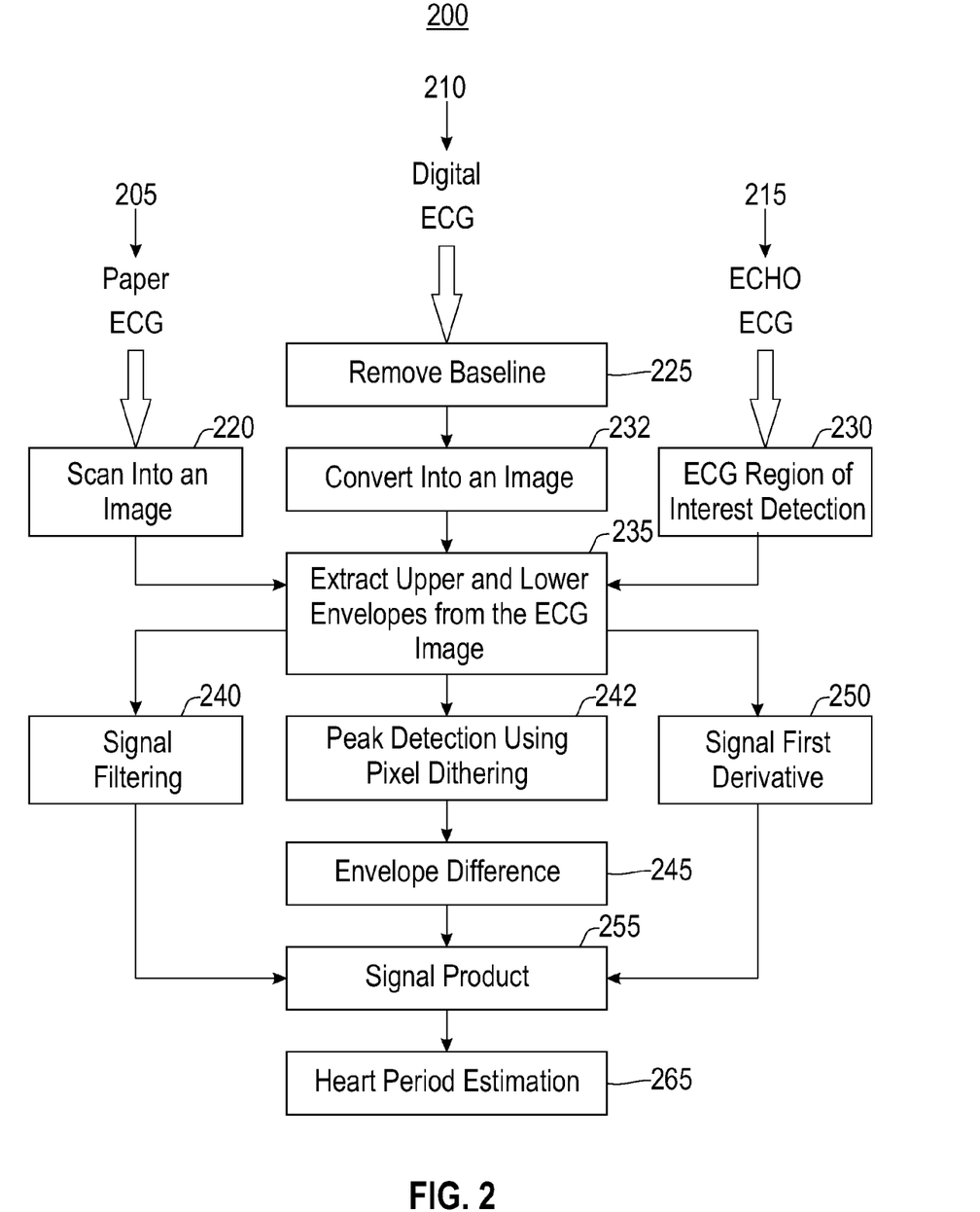
FIG. 2 is a flowchart of an exemplary embodiment of the invention.
Figure 4:
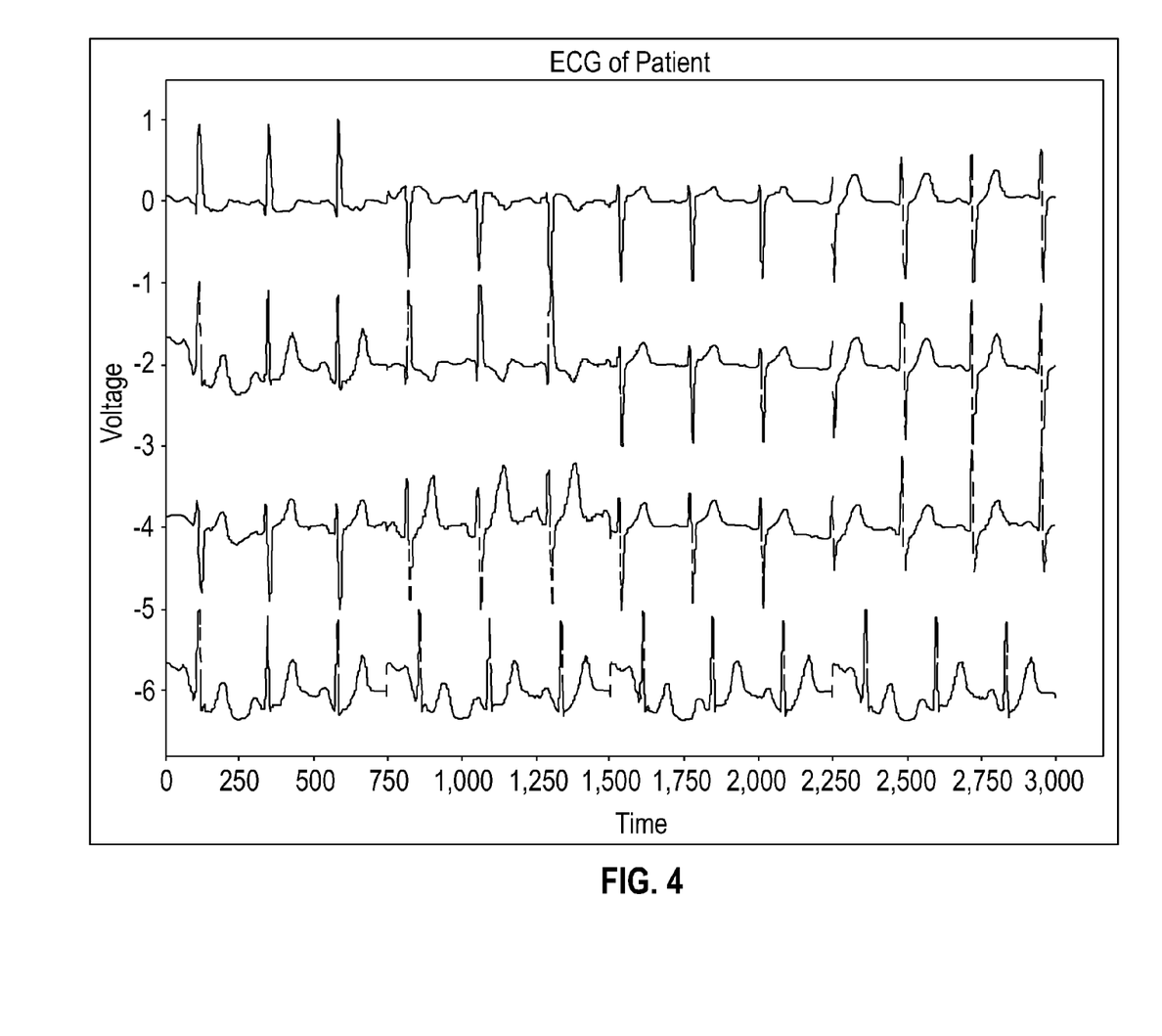
FIG. 4 is a synthetic ECG image generated from a 12-channel digital ECG waveform according to an exemplary embodiment of the invention.
Figure 5A:
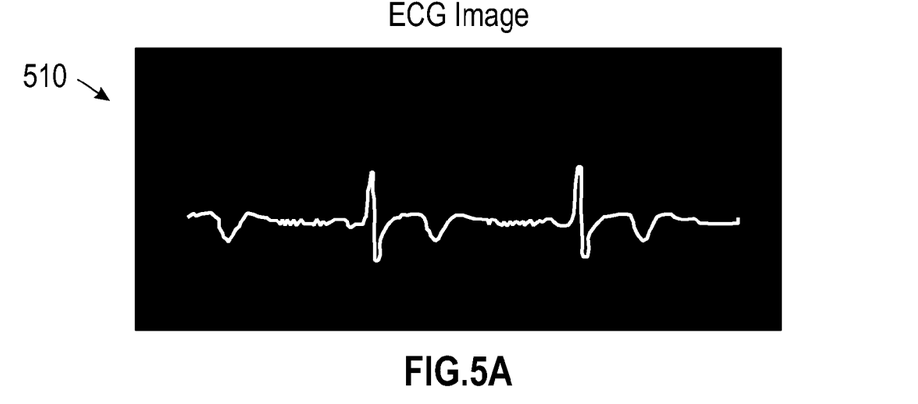
FIG. 5 shows ECG waveforms according to an exemplary embodiment of the invention.
Figure 5B:
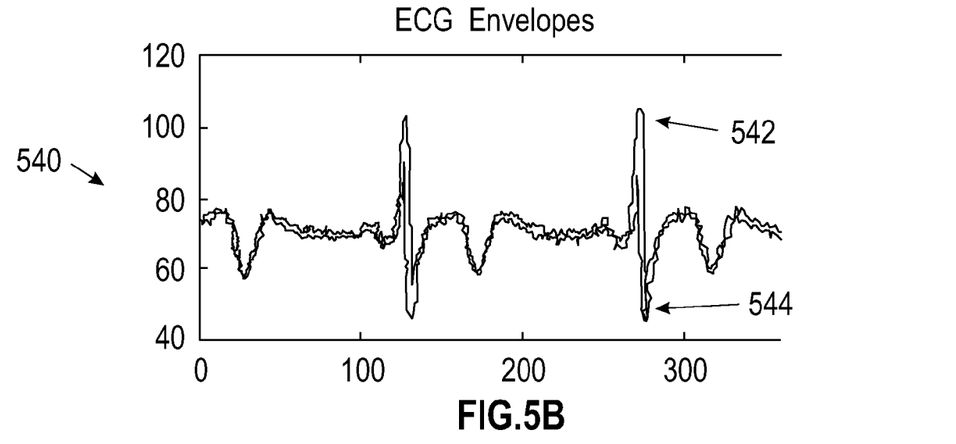
Figure 5C:
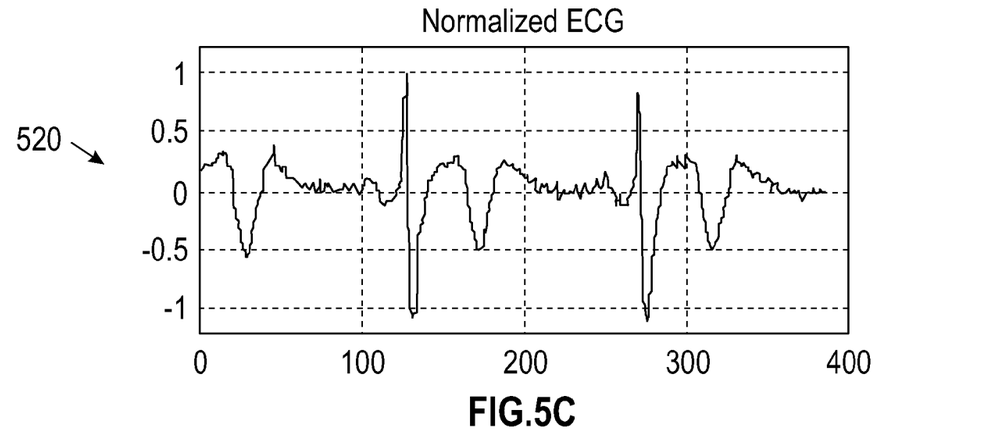
Figure 5D:
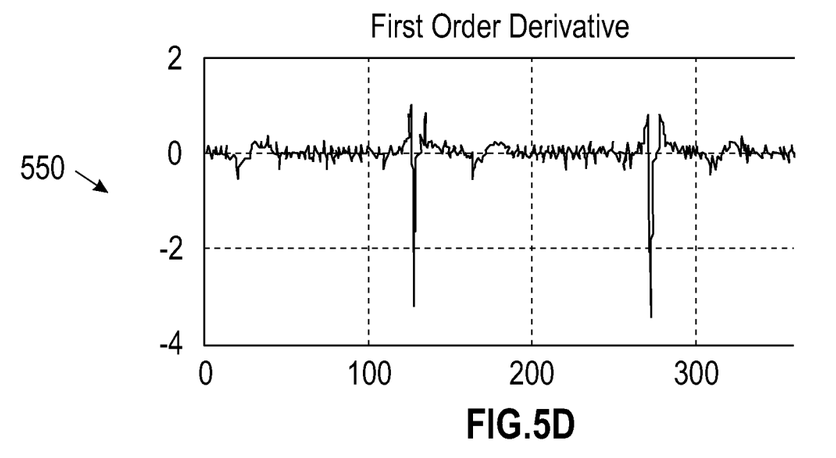
Figure 5E:
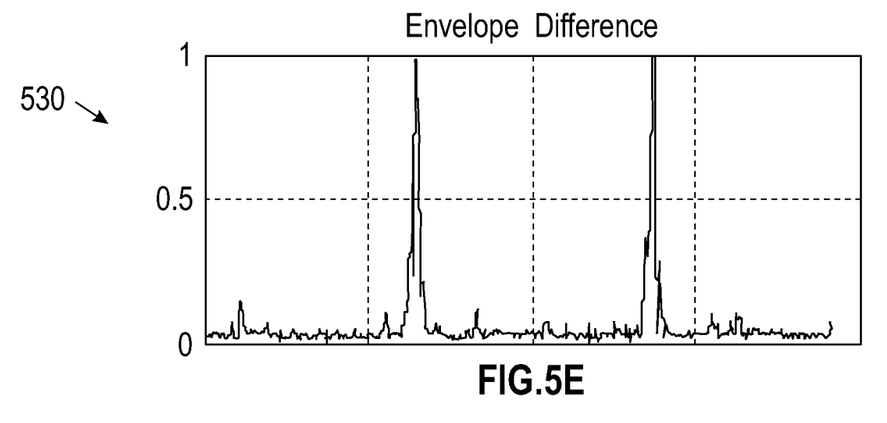
Figure 5F:
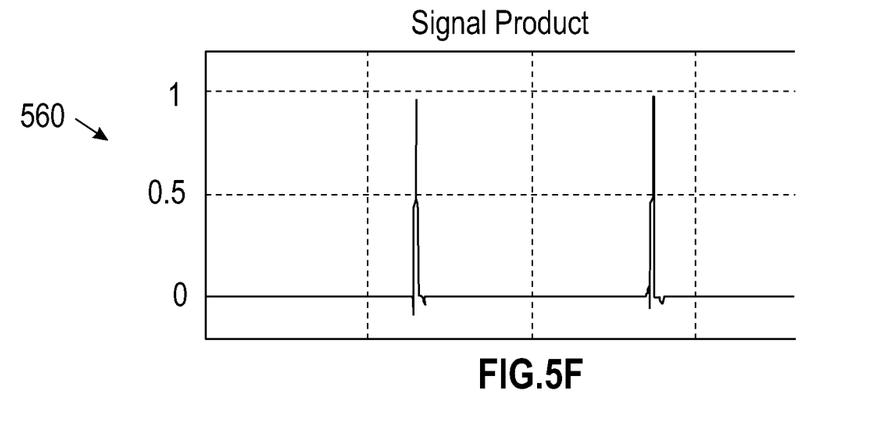

FIG. 2 shows a flowchart 200 of an exemplary embodiment of the invention. As shown in FIG. 2, when an ECG is entered in paper form 205, the paper form may be scanned using processing contained in box 220 into a recording which is converted into a digital (electronic) ECG image. For already existing ECG recordings 210, a wandering baseline may be removed from these digital ECG waveforms (as shown at block 225) before they are synthetically converted into an electronic ECG image by processing contained in box 232. FIG. 4 shows a synthetic ECG image that may be generated from a 12-channel ECG recording. Each channel may be 300 pixels wide in the recording.

For echocardiographic (ECHO ECG) frames 215, they are already in suitable electronic ECG image form and no conversion is necessary.

From the electronic ECG, at least one region of interest (ROI) of an electronic ECG image may be selected. Then, the selected region of interest may be extracted as shown at block 230

At block 235, a step of extracting upper and lower envelopes of an ECG waveform from the selected region of interest of the electronic ECG image may occur.

As shown at block 242, determining an electrocardiogram signal peak from increased thickness at the electrocardiogram signal peak due to pixel dithering may occur. As shown at block 245, the difference of the upper envelope and the lower envelope of the ECG waveform from the electronic ECG image can signify the local maximum and minimum of the ECG waveform in the electronic ECG image. The gap between the two envelopes may increase significantly when the signal reaches a peak or valley.

Figure 3:
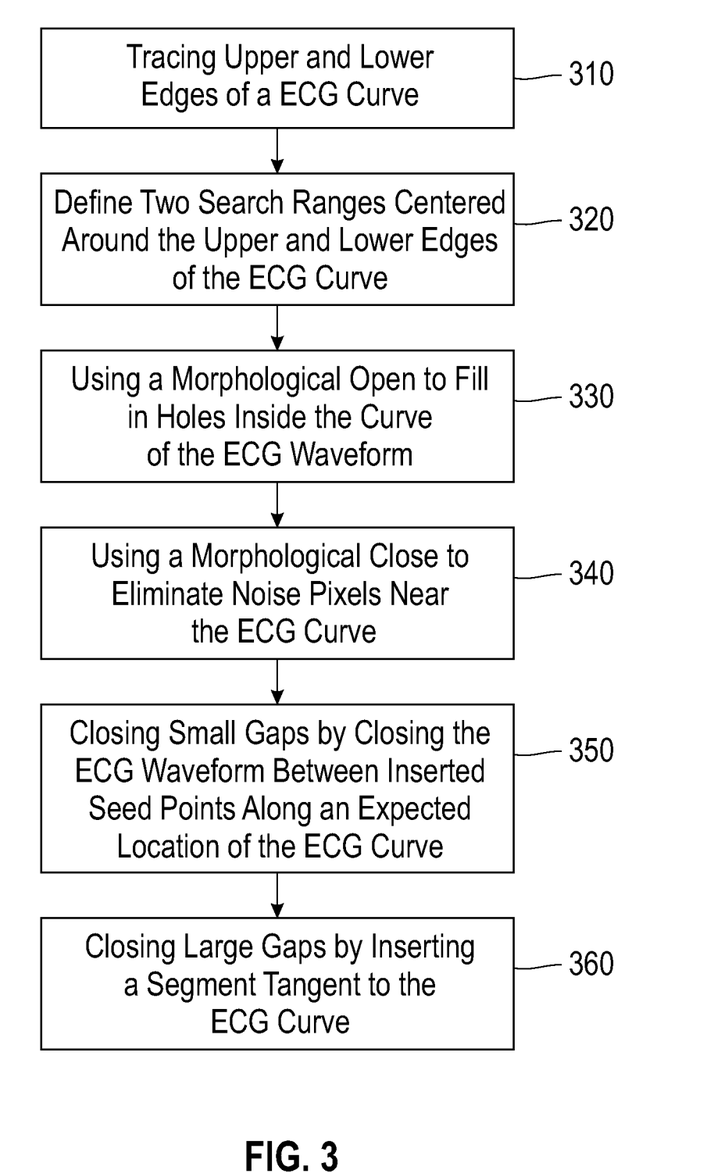
FIG. 3 is a flowchart of an algorithm for extracting upper and lower envelopes of ECG waveforms from electronic ECG images according to an exemplary embodiment of the invention.

Determination of the upper and lower envelopes may be performed, for example, via curve tracing algorithm as shown in FIG. 3. The curve tracing algorithm may initially trace the upper and lower edges of a curve of the ECG waveform in a ECG recording as shown at block 310. The upper edge of the curve may be denoted by $y_u(x)$, and the lower edge of the curve may be denoted by $y_l(x)$.

As shown at block 320, two search ranges may be defined, centered around the upper and lower edges of the electrocardiogram waveform. These values may be designated by:

$$R_u=[y_u(x-1)-W, y_u(x-1)+W];$$

$$R_l=[y_l(x-1)-W, y_l(x-1)+W];$$

where $R_u$ may represent a search range for the upper edge and $R_l$ may represent a search range of the lower edge of the electrocardiogram waveform; and W may represent a search window.

As shown at block 330, a morphological open (erode+ dilate) algorithm may be used to fill in holes inside the curve of the ECG waveform. In the morphological open algorithm, the image of the electronic ECG is first shrunk, then the image region is enlarged. As shown at block 340, a morphological close algorithm may be used to eliminate noise pixels near the curve of the ECG waveform. In the morphological close algorithm, the image of the electronic ECG is first enlarged, then shrunk. As shown at block 350, small gaps may be closed in the ECG waveform between inserted seed points along an expected location of the electrocardiogram waveform. As shown at block 360, large gaps in the ECG waveform may be closed by inserting a segment tangent to the curve of the electrocardiogram waveform;

The upper and lower envelopes may be denoted as $f_u$ and $f_l$ respectively, and ECG waveforms can be derived as the average between the two, i.e., $f=(f_u+f_l)/2$. The difference between the two envelopes may be $f_{diff}=f_u-f_l$.

As shown in FIG. 2 at block 255, in order to determine a peak of an ECG waveform, a signal product may be determined as a product of the filtered electronic ECG image in which a wandering baseline is removed 240, a difference between the upper envelope and the lower envelope 245, and a first derivative of a an ECG waveform signal 250. Then, as shown at block 265, a heart period may be estimated from an average of several intervals between peaks.

FIG. 5 shows ECG waveform signals from electronic ECG images according to an exemplary embodiment of the invention. Block 510 may depict a conventional ECG recording, whether on paper or in digital form. After conversion to electronic form and extraction of upper and lower envelopes of the ECG waveform from the electronic ECG image, an exemplary embodiment of the invention may take the product 560 of three factors to estimate a heart period. The first factor may be a normalized, filtered electronic ECG image in which a wandering baseline has been removed, as shown at block 520. The second factor may be the difference between upper and lower envelopes of the ECG waveform, as shown at block 530. Block 540 shows signals for upper and lower envelopes. An exemplary upper envelope is indicated as graph 542, and an exemplary lower envelope is indicated as graph 544 in block 540. The third factor may be a first order derivative of the ECG waveform, as shown at block 550. A peak of an ECG waveform from an electronic ECG image may be determined from the product 560 of the three factors. The use of a first order derivative of the ECG waveform is advantageous as it may amplify the higher frequencies while attenuating the lower product of the three waveforms.

The signal product may be shown at block 560, and may be expressed as: $S=f*f'*f_{diff}$, where f may be a normalized ECG waveform in which a wandering baseline has been removed, f' may be the first order ECG derivative of the curve of the ECG waveform, which has been derived from the electronic ECG image, and $f_{diff}$ may denote the envelope difference between the upper and lower envelopes of the ECG waveform extracted from the electronic ECG image. Intervals between peaks may next be determined from a plurality of selected regions of electrocardiogram waveforms in electronic ECG images and the period of the ECG waveform in the electronic ECG image can be estimated as an average of intervals between these peaks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more performable instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts, or combinations of special purpose hardware and computer instructions.

It should be understood, of course, that the foregoing relates to exemplary embodiments of the invention and that modifications may be made without departing from the spirit and scope of the invention as set forth in the following claims.

We claim:

1. A method for estimating a heart period using at least one of a plurality of electrocardiogram recordings, comprising:

obtaining the plurality of electrocardiogram recordings generated from a plurality of electrocardiogram sources, wherein the plurality of electrocardiogram sources include a paper form electrocardiogram source, a digital form electrocardiogram source, and an echocardiogram from an echocardiogram source;

utilizing a computer processor to convert a plurality of the electrocardiogram recordings into a plurality of corresponding electronic electrocardiogram images, including removing a wandering baseline from the electrocardiogram recordings prior to conversion of the electrocardiogram recordings to the corresponding electrocardiogram images;

deriving an electrocardiogram waveform from one of the corresponding electronic electrocardiogram images by extracting an upper envelope and a lower envelope of the electrocardiogram waveform from one of the corresponding electronic electrocardiogram images using a curve tracing algorithm;

determining an electrocardiogram signal peak from increased thickness at the electrocardiogram signal peak due to pixel dithering;

determining a difference between an upper envelope and a lower envelope at an electrocardiogram signal peak and at an electrocardiogram low point, which are a local maximum and a local minimum of one of the corresponding electronic electrocardiogram images; and estimating the heart period.

2. The method of claim 1, wherein the curve tracing algorithm for extracting the upper envelope and lower envelope comprises:

tracing upper and lower edges of a curve of the electrocardiogram waveform from one of the electronic electrocardiogram images;

defining two search ranges centered around the upper and lower edges of the curve of the electrocardiogram waveform;

using at least one of: a morphological open algorithm to fill in holes inside the curve of the electrocardiogram waveform and a morphological close algorithm to eliminate noise pixels near the curve of the electrocardiogram waveform;

closing small gaps by closing the electrocardiogram waveform between inserted seed points along an expected location of the derived electrocardiogram waveform; and closing large gaps by inserting a segment tangent to the curve of the electrocardiogram waveform.

3. The method of claim 2, wherein estimating the heart period comprises:

computing a first order derivative of the derived electrocardiogram waveform for amplifying high frequencies of the derived electrocardiogram waveform;

determining a peak of the derived electrocardiogram waveform by taking a product of a filtered electrocardiogram signal from one of the corresponding electronic electrocardiogram images, with a wandering baseline removed, a difference between the upper envelope and the lower envelope of the derived electrocardiogram waveform from each of the at least one of the corresponding electronic electrocardiogram images and the first order derivative of the derived electrocardiogram waveform; and determining an average of intervals between a plurality of detected peaks of the electrocardiogram waveform from at least one region selected from the electronic electrocardiogram image.

4. The method of claim 3, further comprising obtaining the plurality of electrocardiogram recordings generated from a plurality of electrocardiogram sources.

5. The method of claim 4, further comprising removing noise from the corresponding electronic electrocardiogram images.

6. The method of claim 5, further comprising outputting the determined heart period on a display.

7. The method of claim 6, wherein at least one of the electrocardiogram sources comprises a paper form electrocardiogram source.

8. The method of claim 7, further comprising scanning the paper form of said electrocardiogram source into at least one electronic electrocardiogram image.

9. The method of claim 6, wherein at least one of the electrocardiogram sources comprises a digital form electrocardiogram source.

10. The method of claim 6, wherein at least one of the electrocardiogram sources comprises an echocardiogram from an echocardiogram source.

* * * * *